US012324847B2

United States Patent
Pan et al.

(10) Patent No.: US 12,324,847 B2
(45) Date of Patent: *Jun. 10, 2025

(54) ORAL CARE COMPOSITIONS

(71) Applicant: Colgate-Palmolive Company, New York, NY (US)

(72) Inventors: Guisheng Pan, Philadelphia, PA (US); Lin Fei, Kendall Park, NJ (US); Suman Chopra, Monroe, NJ (US)

(73) Assignee: Colgate-Palmolive Company, New York, NY (US)

( * ) Notice: Subject to any disclaimer, the term of this patent is extended or adjusted under 35 U.S.C. 154(b) by 65 days.

This patent is subject to a terminal disclaimer.

(21) Appl. No.: 17/472,241

(22) Filed: Sep. 10, 2021

(65) Prior Publication Data

US 2021/0401692 A1 Dec. 30, 2021

Related U.S. Application Data

(63) Continuation of application No. 15/827,571, filed on Nov. 30, 2017, now Pat. No. 11,141,364.

(51) Int. Cl.
*A61K 8/22* (2006.01)
*A61K 8/02* (2006.01)
*A61K 8/36* (2006.01)
*A61K 8/81* (2006.01)
*A61K 8/86* (2006.01)
*A61K 8/90* (2006.01)
*A61Q 11/00* (2006.01)

(52) U.S. Cl.
CPC .............. *A61K 8/22* (2013.01); *A61K 8/0204* (2013.01); *A61K 8/361* (2013.01); *A61K 8/8176* (2013.01); *A61K 8/86* (2013.01); *A61K 8/90* (2013.01); *A61Q 11/00* (2013.01)

(58) Field of Classification Search
CPC ........ A61K 8/22; A61K 8/0204; A61K 8/361; A61K 8/8176; A61K 8/90; A61K 8/86; A61Q 11/00
See application file for complete search history.

(56) References Cited

U.S. PATENT DOCUMENTS

| 4,307,076 A | 12/1981 | Harvey et al. |
| 4,983,380 A | 1/1991 | Yarborough |
| 5,804,165 A | 9/1998 | Arnold |
| 5,817,294 A | 10/1998 | Arnold |
| 8,591,868 B2 | 11/2013 | Chopra et al. |
| 8,900,557 B2 | 12/2014 | Ramirez |
| 10,548,826 B2 * | 2/2020 | Yuan ...................... A61K 8/365 |
| 2007/0071695 A1 | 3/2007 | Chopra et al. |
| 2007/0122360 A1 * | 5/2007 | Oniki ................... A61K 8/8158 424/53 |
| 2016/0303011 A1 * | 10/2016 | Pan ....................... A61K 8/342 |
| 2018/0093113 A1 | 4/2018 | Schade et al. |

FOREIGN PATENT DOCUMENTS

| CN | 106236607 | 12/2016 | |
| GB | 1470581 | 4/1977 | |
| WO | WO-2010068430 A2 * | 6/2010 | ............... A61K 8/25 |
| WO | 2011/040909 | 4/2011 | |
| WO | WO-2014033230 A1 * | 3/2014 | ............... A23D 7/04 |
| WO | WO-2014092736 A1 * | 6/2014 | ........... A61K 8/0241 |
| WO | 2016/044805 | 3/2016 | |

OTHER PUBLICATIONS

WO-2014033230-A1 Translation (Year: 2014).*
Amden, 2005, "Oral Care Mints," Database Mintel GNPD AN: 10226024.
International Search Report and Written Opinion of the International Searching Authority in International Application No. PCT/US2017/063924, mailed Apr. 16, 2018.
Lippert, 2013, "Monographs Oral Science" Epub, vol. 23:1-14.
Lornamead, 2003, "Brush-On Tooth Whitening Gel," Database Mintel GNPD AN: 10135058.
NaturalMax, 2001, "Tooth Whitening Tablets," Database Mintel GNPD AN: 10098556.
CAO Jiaxin et al., Colloid Theory and Toothpaste Production, Light Industry Press, 1st Ed., Apr. 1981, p. 150.
Song, Xiaoping et al., Manual of Practical Chemical Formula (VIII), Sichuan Science and Technology Press, 1st Ed., printed Jan. 1997, p. 533.

* cited by examiner

*Primary Examiner* — Snigdha Maewall

(57) ABSTRACT

Oral care compositions and methods for the same are provided herein. The oral care composition may include an orally acceptable vehicle, a peroxide whitening agent, and one or more gelling agents. The gelling agents may include a fatty acid. The gelling agents may be free or substantially free of fatty alcohols. The gelling agents may include at least one of palmitic acid, stearic acid, or mixtures thereof.

16 Claims, No Drawings

ORAL CARE COMPOSITIONS

CROSS REFERENCE TO RELATED APPLICATIONS

This application is a continuation of U.S. application Ser. No. 15/827,571, filed Nov. 30, 2017, the content of which is incorporated herein by reference in its entirety.

BACKGROUND

Conventional oral care products (e.g., toothpastes, whitening gels, whitening trays, etc.) and peroxide whitening agents thereof are often utilized to whiten teeth. For example, conventional whitening toothpastes including hydrogen peroxide are often utilized to oxidize chromophores bound to surfaces of teeth to thereby whiten the teeth. While whitening toothpastes including hydrogen peroxide have proven to be effective, the peroxides contained therein are often unstable (e.g., reactive) and subject to degradation or reactivity with other components of the toothpastes. For example, the hydrogen peroxide in whitening toothpastes are often highly reactive to conventional thickeners or gelling agents, thereby reducing the whitening efficacy of the toothpastes.

In view of the foregoing, conventional oral care products may often be provided as a two-component whitening system to separate the hydrogen peroxide from potentially reactive components until the time of use when they may be mixed. While conventional two-component whitening systems have been able to prevent reactivity between the hydrogen peroxide and other components of the toothpastes, the implementation of these two-component whitening systems are cost-prohibitive. Further, the two-component whitening systems may often exhibit decreased mixing efficiency, which results in heterogeneous mixtures.

What is needed, then, are improved single phase oral care compositions including peroxide whitening agents having increased peroxide stability.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

Embodiments of the disclosure may provide an oral care composition including an orally acceptable vehicle, a peroxide whitening agent, and one or more gelling agents. The gelling agents may include a fatty acid.

In at least one embodiment, the fatty acid includes a C12-C28 fatty acid.

In at least one embodiment, the fatty acid includes at least one of lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, linoleic acid, arachidonic acid, palmitoleic acid, oleic acid, or mixtures thereof.

In at least one embodiment, the fatty acid includes a saturated fatty acid.

In at least one embodiment, the fatty acid includes an unsaturated fatty acid.

In at least one embodiment, the fatty acid includes at least one of palmitic acid, stearic acid, or mixtures thereof.

In at least one embodiment, the gelling agents are present in an amount of from about 1 weight % to about 50 weight %.

In at least one embodiment, the gelling agents may be substantially free of fatty alcohols.

In at least one embodiment, the oral care composition may include fatty alcohols in an amount of less than 5.0 weight %, less than 3.0 weight %, less than 1.0 weight %, less than 0.1 weight %, less than 0.05 weight %, less than 0.01 weight %, less than 0.005 weight %, or less than 0.0001 weight %, based on a total weight of the oral care composition.

In at least one embodiment, the oral care composition may be substantially free of fatty alcohols.

In at least one embodiment, the oral care composition may include water in an amount of less than 5.0 weight %, less than 3.0 weight %, or less than 1.0 weight %, optionally, the oral care composition is anhydrous.

In at least one embodiment, the oral care composition may be a single phase oral care composition.

In at least one embodiment, the peroxide whitening agent may include hydrogen peroxide or one or more sources of hydrogen peroxide.

In at least one embodiment, the peroxide whitening agent includes at least one of hydrogen peroxide, a cross-linked PVP hydrogen peroxide complex, peroxides of alkali and alkaline earth metals, organic peroxy compounds, peroxy acids, pharmaceutically-acceptable salts thereof, or mixtures thereof.

In at least one embodiment, the peroxide whitening agent may be a cross-linked PVP hydrogen peroxide complex.

Embodiments of the disclosure may provide a method for whitening teeth. The method may include contacting any of the oral care compositions disclosed herein with surfaces of the teeth.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

The present inventors have surprisingly and unexpectedly discovered that fatty acids as thickening or gelling agents are compatible with peroxide whitening agents in oral care compositions. Particularly, that conventional thickening agents may be replaced with fatty acids to provide similar or comparable compatibility. The present inventors have also surprisingly and unexpectedly discovered a method for increasing peroxide stability in a single phase oral care product and/or a single phase oral care composition thereof. The method for increasing peroxide stability may include replacing conventional thickening agents with fatty acids. The method may also include preparing an oral care composition that is free or substantially free of fatty alcohols. It should be appreciated that the increased peroxide stability in the oral care products and/or oral care compositions thereof may be achieved without encapsulations and/or film-type materials to enhance the stability thereof.

Compositions disclosed herein may be or include an oral care product and/or an oral care composition thereof. The oral care composition may be a non-aqueous oral care composition, such as a non-aqueous dentifrice or toothpaste. The oral care composition may include an orally acceptable vehicle, a peroxide whitening agent, and one or more gelling agents. The gelling agents may be or include, but are not limited to, fatty acids. In at least one implementation, the gelling agents are free or substantially free of fatty alcohols. As used herein, "free of fatty alcohols" or "substantially free of fatty alcohols" may refer to a composition that contains fatty alcohols in an amount of less than 5.0 weight %, less than 3.0 weight %, less than 1.0 weight %, less than 0.1 weight %, less than 0.05 weight %, less than 0.01 weight %, less than 0.005 weight %, or less than 0.0001 weight %, based on a total weight of the oral care composition.

The oral care composition prior to use may be anhydrous. For example, the oral care composition may be free or substantially free of water. As used herein, "free of water" or "substantially free of water" may refer to a composition that contains water in an amount of less than 5.0 weight %, less than 3.0 weight %, less than 1.0 weight %, less than 0.1 weight %, less than 0.05 weight %, less than 0.01 weight %, less than 0.005 weight %, or less than 0.0001 weight %, based on a total weight of the oral care composition. The oral care composition prior to use may have a "low water content". As used herein, "low water content" may refer to a composition that contains water in an amount greater than about 5 weight % and less than about 7 weight % or less than about 10 weight %.

The oral care product or the oral care composition thereof may be a single phase oral care product or single phase oral care composition. For example, all the components of the oral care product or the oral care composition thereof may be maintained together with one another in a single phase and/or vessel. For example, the all the components of the oral care product or the oral care composition thereof may be maintained in a single phase, such as a single homogenous phase. The single homogenous may be an anhydrous formulation or an anhydrous composition.

The oral care composition may be or form at least a portion of one or more oral care products. The oral care composition may include or be combined with an orally acceptable vehicle to form the oral care product (e.g., the toothpaste). Illustrative oral care products may include, but are not limited to, a toothpaste (dentifrice), a prophylactic paste, a tooth powder, a tooth polish, a tooth gel (e.g., a whitening gel), a chewing gum, a lozenge, a mouthwash, a whitening strip, a paint-on gel, varnish, veneer, and tube, syringe or dental tray comprising a gel or paste, or a gel or paste coated on an application support such as dental floss or a toothbrush (e.g., a manual, electric, sound, a combination thereof or ultrasound toothbrush). In a typical implementation, the oral care composition may be or may form at least a portion of a toothpaste.

In at least one implementation, the orally acceptable vehicle may include one or more humectants. Illustrative humectants may be or include, but are not limited to, glycerin, propylene glycol, polyethylene glycol, block copolymers of ethylene oxide (EO) and propylene oxide (PO), and combinations thereof. Illustrative block copolymers of ethylene oxide (EO) and propylene oxide (PO) may be or include, but are not limited to, PLURONIC® L1, PLURONIC® L43, PLURONIC® L10, PLURONIC® L44, PLURONIC® 10R5, PLURONIC® 17R4, PLURONIC® L25R4, PLURONIC® P84, PLURONIC® P65, PLURONIC® P104, PLURONIC® P105, and the like, and combinations thereof, all of which are commercially available from BASF of Mount Olive, NJ. In a preferred implementation, the orally acceptable vehicle may be or include, but is not limited to, propylene glycol.

The orally acceptable vehicle or the humectant (e.g., propylene glycol) thereof may be present in an amount of from 5 weight % to about 60 weight %, based on a total weight of the oral care composition. For example, the orally acceptable vehicle or the humectant thereof may be present in an amount of from about 5 weight %, about 10 weight %, about 15 weight %, or about 20 weight % to about 25 weight %, about 30 weight %, about 35 weight %, about 40 weight %, about 45 weight %, about 50 weight %, about 55 weight %, or about 60 weight %. In another example, the orally acceptable vehicle or the humectant thereof may be present in an amount of from about 5 weight % to about 60 weight %, about 10 weight % to about 55 weight %, about 15 weight % to about 50 weight %, about 20 weight % to about 25 weight %, about 20 weight % to about 40 weight %, about 20 weight % to about 35 weight %, about 20 weight % to about 30 weight %, or about 20 weight % to about 25 weight %. In an exemplary implementation, the orally acceptable vehicle or the humectant thereof may be present in an amount of about 20 weight % to about 30 weight %, preferably about 20 weight % to about 25 weight %, and more preferably about 22 weight % to about 25 weight %. In a preferred implementation, the orally acceptable vehicle or the humectant thereof may be present in an amount of about 22 weight % to about 25 weight % or about 23 weight %.

The oral care product or the composition thereof may include one or more peroxide whitening agents. The peroxide whitening agents may be or include, but are not limited to, hydrogen peroxide or one or more sources of hydrogen peroxide. For example, the peroxide whitening agents may be hydrogen peroxide and/or hydrogen peroxide releasing substances. The one or more sources of hydrogen peroxide may be or include any compound or material configured to release hydrogen peroxide. Preferably, the peroxide whitening agents include, but are not limited to, solid peroxide whitening agents and bound peroxide whitening agents that are substantially anhydrous oxygen generating compounds. Solid peroxide whitening agents may include, but are not limited to, peroxides and persulfates. Exemplary peroxide phases include hydroperoxides, hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include, but are not limited to, lithium peroxide, potassium peroxide, sodium peroxide, magnesium peroxide, calcium peroxide, barium peroxide, and mixtures thereof. Organic peroxy compounds include, but are not limited to, urea peroxide, glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include, but are not limited to, organic peroxy acids such as alkyl peroxy acids, and monoperoxyphthalate and mixtures thereof, as well as inorganic peroxy acid salts such as and perborate salts of alkali and alkaline earth metals such as lithium, potassium, sodium, magnesium, calcium and barium, and mixtures thereof. Preferred solid peroxides are sodium perborate, urea peroxide, and mixtures thereof. The peroxide whitening agents may be preferably bound. For example, peroxide may be bound to a polymer such as PVP (poly(N-vinylpyrrolidone). Suitable PVP complexes are disclosed, for example, in U.S. Pat. No. 5,122,370, the contents of which are incorporated herein by reference. In some implementations, it may be desirable to use any known peroxide whitening agent except sodium percarbonate and/or any of the percarbonate salts. The sources of hydrogen peroxide or peroxide whitening agents may also be or include, but are not limited to, PEROXYDONE™ XL 10 complex or POLYPLASDONE® XL 10F, which are commercially available from Ashland Inc. of Covington, KY. In a typical implementation, the source of hydrogen peroxide includes a cross-linked PVP hydrogen peroxide complex.

The amount or concentration of the source of hydrogen peroxide may vary widely. In at least one example, the source of hydrogen peroxide may be present in an amount that provides a concentration of hydrogen peroxide of less than or equal to 4 weight %, less than or equal to 3.5 weight %, less than or equal to 3 weight %, less than or equal to 2.5 weight %, less than or equal to 2 weight %, or less than or equal to 1.5 weight %, based on a total weight of the oral care product or the composition thereof. In at least one implementation, the source of hydrogen peroxide may be present in an amount greater than or equal to 1 weight % and less than or equal to 30 weight %, based on a total weight of the oral care composition. For example, the source of hydrogen peroxide may be present in an amount of from about 1 weight %, about 3 weight %, about 5 weight %, about 7 weight %, about 9 weight %, about 11 weight %, about 13 weight %, or about 15 weight % to about 17 weight %, about 19 weight %, about 21 weight %, about 23 weight %, about 25 weight %, about 27 weight %, about 29 weight %, or about 30 weight %. In another example, the source of hydrogen peroxide may be present in an amount of from about 1 weight % to about 30 weight %, about 3 weight % to about 29 weight %, about 5 weight % to about 27 weight %, about 7 weight % to about 25 weight %, about 9 weight % to about 23 weight %, about 11 weight % to about 21 weight %, about 13 weight % to about 19 weight %, or about 15 weight % to about 17 weight %. In a preferred implementation, the source of hydrogen peroxide is a cross-linked PVP complexed with hydrogen peroxide, and is present in an amount of from about 8 weight % to about 14 weight %, preferably about 10 weight % to about 12 weight %, and more preferably about 11 weight %.

The oral care product or the composition thereof may include one or more thickening or gelling agents capable of or configured to thicken the oral care product or the composition thereof. Illustrative thickening or gelling agents may be or include, but are not limited to, carbomers, also known as carboxyvinyl polymers, carrageenans, also known as Irish moss and more particularly i-carrageenan (iota-carrageenan), high molecular weight polyethylene glycols (such as CARBOWAX®, available from The Dow Chemical Company), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal and/or fumed silica, cross-linked polyvinylpyrrolidone (PVP), and the like, and mixtures and combinations thereof.

Illustrative thickening agents may also be or include, but are not limited to, one or more fatty acids. As used herein, the term "fatty acid" may refer to an aliphatic monocarboxylic acid. The fatty acid may be or include an unsaturated linear and/or a saturated linear fatty acid. In at least one implementation, the fatty acid may be or include one or more unsaturated linear or saturated linear C12-C28 fatty acids. It should be appreciated that the oral care product or the composition thereof may include any one or more fatty acids within the indicated carbon number range. For example, the thickening agents in the oral care product or the oral care composition thereof may be or include lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, linoleic acid, arachidonic acid, palmitoleic acid, oleic acid, and the like, and mixtures or combinations thereof. In an exemplary implementation the oral care product or the composition thereof includes palmitic acid and/or stearic acid as thickening agents.

The amount or concentration of the thickening agents may vary widely. In at least one example, the thickening agents may be present in an amount greater than or equal to 0.1 weight % and less than or equal to 50 weight %. For example, the thickening agents may be present in an amount of from about 0.1 weight %, about 0.2 weight %, about 0.4 weight %, about 0.6 weight %, about 0.8 weight %, about 1 weight %, about 1.5 weight %, about 2 weight %, about 2.5 weight %, or about 3 weight % to about 3.5 weight %, about 4 weight %, about 4.5 weight %, about 5 weight %, or about 5.5 weight %. In another example, the thickening agents may be present in an amount of from about 1 weight % to about 5.5 weight %, about 1.5 weight % to about 5 weight %, about 2 weight % to about 4.5 weight %, about 2.5 weight % to about 4 weight %, or about 3 weight % to about 3.5 weight %. In another example, the thickening agents may be present in an amount of from about 1 weight %, about 2 weight %, about 3 weight %, about 4 weight %, about 5 weight %, about 6 weight %, about 7 weight %, about 8 weight %, about 9 weight %, or about 10 weight % to about 15 weight %, about 20 weight %, about 25 weight %, about 30 weight %, about 35 weight %, about 40 weight %, about 45 weight %, or about 50 weight %.

The oral care product or the composition thereof may include an abrasive system including one or more abrasives. As used herein, the term "abrasive" may also refer to materials commonly referred to as "polishing agents". Illustrative abrasives may include, but are not limited to, phosphate salts (e.g., insoluble phosphate salts), such as sodium metaphosphate, potassium metaphosphate, calcium pyrophosphate, magnesium orthophosphate, trimagnesium orthophosphate, tricalcium phosphate, dicalcium phosphate dihydrate, anhydrous dicalcium phosphate and the like, calcium carbonate, magnesium carbonate, hydrated alumina, silica, zirconium silicate, aluminum silicate including calcined aluminum silicate, polymethyl methacrylate, and the like, and mixtures or combinations thereof.

Illustrative abrasives may also be or include, but are not limited to, those previously considered to be incompatible in a peroxide containing formulation ("a peroxide-incompatible abrasive"). As used herein, "a peroxide-incompatible abrasive" may refer to an abrasive that substantially reacts with hydrogen peroxide in an aqueous medium (e.g., solution) so as to reduce a whitening efficacy of the medium. "A peroxide-incompatible abrasive" may also refer to an abrasive that reacts with hydrogen peroxide in a single phase oral care composition (e.g., toothpaste) such that the amount of hydrogen peroxide present in the oral care composition after exposure to accelerated aging conditions for a period of 1, 2, 3, 4, 5, 10, 15, or 20 weeks is reduced by at least 0.5%, at least 0.6%, at least 0.7%, at least 0.8%, at least 0.9%, at least 1.0%, at least 1.1%, at least 1.2%, at least 1.3%, at least 1.4%, at least 1.5%, at least 1.6%, at least 1.7%, at least 1.8%, at least 1.9%, at least 2.0%, at least 2.5%, at least 3.0%, at least 3.5%, at least 4.0%, at least 4.5%, at least 5.0%, at least 5.5%, at least 6.0%, at least 6.5%, at least 7.0%, at least 7.5%, at least 8.0%, at least 8.5%, at least 9.0%, at least 9.5%, at least 10.0%, at least 10.5%, at least 11.0%, at least 11.5%, at least 12.0%, at least 12.5%, at least 13.0%, at least 13.5%, at least 14.0%, at least 14.5%, or at least 15%. Illustrative "peroxide-incompatible abrasives" may be or include, but are not limited to, silica, dicalcium phosphate hydrate, calcium carbonate, hydroxyapatite, calcium phosphate, and the like.

The amount or concentration of the abrasive system and abrasives thereof may vary widely. In at least one implementation, the amount or concentration of the abrasives may be from greater than 0 weight % to about 40 weight %, based on a total weight of the oral care product or the composition thereof. For example, the amount of the abrasives present in the oral care composition may be from greater than 0 weight %, about 2 weight %, about 4 weight %, about 6 weight %, about 8 weight %, about 10 weight %, about 12 weight %, about 14 weight %, about 16 weight %, about 18 weight %, or about 19 weight % to about 21 weight %, about 22 weight %, about 24 weight %, about 26 weight %, about 28 weight %, about 30 weight %, about 32 weight %, about 34 weight %, about 36 weight %, about 38 weight %, or about 40 weight %. In another example, the amount of the abrasives present in the oral care composition may be from greater than 0 weight % to about 40 weight %, about 2 weight % to about 38 weight %, about 4 weight % to about 36 weight %, about 6 weight % to about 34 weight %, about 8 weight % to about 32 weight %, about 10 weight % to about 30 weight %, about 12 weight % to about 28 weight %, about 14 weight % to about 26 weight %, about 16 weight % to about 24 weight %, about 18 weight % to about 22 weight %, or about 19 weight % to about 21 weight %. In a preferred implementation, the amount of the abrasives present in the oral care composition may be from about 18 weight % to about 22 weight %, preferably about 19 weight % to about 21 weight %, or more preferably about 20 weight %, based on a total weight of the oral care product or the composition thereof.

In at least one implementation, the oral care products and/or the oral care composition thereof may be free or substantially free of fluoride (e.g., soluble fluoride salts). In another implementation, the oral care products and/or the oral care composition thereof may further include fluoride, such as one or more fluoride ion sources (e.g., soluble fluoride salts). A wide variety of fluoride ion-yielding materials may be employed as sources of soluble fluoride. Examples of suitable fluoride ion-yielding materials may be found in U.S. Pat. No. 3,535,421 to Briner et al., U.S. Pat. No. 4,885,155 to Parran, Jr. et al., and U.S. Pat. No. 3,678,154 to Widder et al., the disclosures of which are incorporated herein by reference. Illustrative fluoride ion sources include, but are not limited to, fluoride, stannous fluoride, sodium fluoride, potassium fluoride, sodium monofluorophosphate, fluorosilicate salts, such as sodium fluorosilicate and ammonium fluorosilicate, amine fluoride, ammonium fluoride, and combinations thereof. In a typical implementation, the fluoride ion source includes sodium monofluorophosphate. The amount of the fluoride ion source in the oral care composition may be greater than 0 weight % and less than 0.8 wt %, less than 0.7 wt %, less than 0.6 wt %, less than 0.5 wt %, or less than 0.4 wt %. The fluoride ion sources may be present in an amount sufficient to provide a total of about 100 to about 20,000 ppm, about 200 to about 5,000 ppm, or about 500 to about 2,500 ppm fluoride ions.

It should be appreciated to one having ordinary skill in the art, that the oral care products and/or the oral care composition thereof may include other additional ingredients/components. For example, the oral care products and/or the oral care composition thereof may include anti-caries agents, desensitizing agents, viscosity modifiers, diluents, pH modifying agents, humectants, mouth feel agents, sweetening agents, flavor agents, colorants, preservatives, and the like, and combinations and mixtures thereof. It should further be appreciated by one having ordinary skill in the art that while general attributes of each of the above categories of materials may differ, there may be some common attributes and any given material may serve multiple purposes within two or more of such categories of materials.

In at least one implementation, the additional ingredients/components may include one or more active materials configured to prevent and/or treat one or more conditions and/or disorders of the oral cavity. For example, the one or more active materials may be configured to prevent and/or treat one or more conditions and/or disorders of hard and/or soft tissue of the oral cavity. The active materials may also be configured to prevent and/or treat one or more physiological disorders and/or conditions, and/or provide a cosmetic benefit to the oral cavity.

In at least one implementation, the oral care products or the oral care composition thereof may include an anticalculus agent. Generally, anticalculus agents may not be compatible with some oral care composition, however, implementations of the present disclosure may incorporate anticalculus agents and the oral care composition into a single phase oral care product. Illustrative anticalculus agents may include, but are not limited to, phosphates and polyphosphates (e.g., pyrophosphates), polyaminopropane-sulfonic acid (AMPS), hexametaphosphate salts, zinc citrate trihydrate, polypeptides, polyolefin sulfonates, polyolefin phosphates, diphosphonates. In a typical implementation, the anticalculus agents include tetrasodium pyrophosphate (TSPP), sodium tripolyphosphate (STPP), or a combination thereof.

The oral care products or the oral care composition thereof may include an antioxidant. Any orally acceptable antioxidant may be used, including, but not limited to, butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and the like, and combinations and mixtures thereof.

The present disclosure may provide methods for increasing peroxide stability in an oral care product and the oral care composition thereof. The method may include at least partially preventing the peroxide whitening agent or peroxides from reacting with other components (e.g., abrasives) of the oral care composition under accelerated aging conditions (e.g., temperature from about 40° C. to about 50° C.). The method may also include at least partially preventing the peroxide whitening agent or peroxides from reacting with other components of the oral care composition for at least three months under accelerated aging conditions. The method may further include maintaining viability, stability, and/or compatibility with the peroxide whitening agent under accelerated aging conditions. For example, the method may include maintaining viability, stability, and/or compatibility with the peroxide whitening agent for at least three months.

It should be appreciated that all ingredients for use in the compositions described herein are orally acceptable. As used herein, the expression "orally acceptable" may define an ingredient that is present in a composition as described in an amount and form that does not render the composition unsafe for use in the oral cavity.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

The stability of oral care compositions (1)-(3) including a peroxide whitening agent, namely, a cross-linked PVP complexed with hydrogen peroxide, and varying thickening agents was evaluated. Particularly, the stability of thickening agents palmitic acid and stearic acid with respect to the cross-linked PVP complexed with hydrogen peroxide was evaluated. The oral care compositions (1)-(3) were prepared by combining the ingredients/components according to Table 1. As indicated in Table 1, oral care composition (1) was a control and included no fatty acids, oral care composition (2) included palmitic acid, and oral care composition (3) included stearic acid. It should be appreciated that oral care compositions including the corresponding fatty alcohols of palmitic acid and stearic acid, namely, cetyl alcohol and stearyl alcohol, were evaluated, but testing was stopped after the first day, as the compositions exhibited excessive bloating that caused the testing tubes to burst.

TABLE 1

| Oral Care Compositions (1)-(3) | | | |
|---|---|---|---|
| Ingredient | (1) | (2) | (3) |
| Palmitic Acid (CH$_3$(CH$_2$)$_{14}$COOH) | — | 5% | — |
| Stearic Acid (CH$_3$(CH$_2$)$_{16}$COOH) | — | — | 5% |
| Cross-linked PVP complexed with hydrogen peroxide | 16.5% | 16.5% | 16.5% |
| Excipients (Orally Acceptable Vehicle, Thickener, Viscosity Control Agent, Abrasives, Polymer, Anticalculus and/or Anti-tartar agent, Fluoride Ion Source, Flavor, Surfactants, Sweeteners, Fluoride, Antioxidants, Anticalculus and Tartar Control Agents, Polymers) | Q.S. | Q.S. | Q.S. |
| Total | 100% | 100% | 100% |

The stability of the oral care compositions (1)-(3) were evaluated under accelerated aging conditions. Particularly, each of the oral care compositions (1)-(3) were aged in an incubator maintained at 49° C. and 75% Relative Humidity (RH) for 2 months. To test the stability via bloating, each of the oral care compositions (1)-(3) was disposed in a standard crimped dentifrice tube. Each of the tubes were marked approximately 40 mm from the bottom of a crimp of the tube to indicate the point of measurement. Measurements of the bloating were conducted by measuring the respective width of each of the tubes with a digital caliper positioned at the point of measurement and at an angle parallel to the crimp of the tube. The results of the stability of the oral care compositions are summarized in Table 2.

TABLE 2

| Bloating of Oral Care Compositions (1)-(3) After Aging at 49° C. for 2 Months | | | |
|---|---|---|---|
| | (1) Control | (2) Palmitic Acid | (3) Stearic Acid |
| Bloating (mm) | 3.54 | 3.28 | 3.81 |
| Stand deviation (mm) | 0.9 | 2.4 | 1.3 |

As indicated in Table 2, both the oral care compositions (2) and (3) were comparable with the control, and there was no statistical difference among the three oral care compositions (1)-(3) tested. The similar results indicated minimal bloating or increased compatibility between the fatty acids and the peroxide. Accordingly, it was surprisingly and unexpectedly discovered that fatty acids as thickening or gelling agents are compatible with peroxide whitening agents in the oral care compositions. This was further surprising and unexpected, as the corresponding fatty alcohols of palmitic acid and stearic acid, namely, cetyl alcohol and stearyl alcohol, were evaluated, but failed when the respective crimped dentifrice tubes burst due to excessive bloating within the first day.

Example 2

The stability of oral care compositions (4)-(6) including a peroxide whitening agent, namely, a cross-linked PVP complexed with hydrogen peroxide, and varying thickening agents was evaluated via phase separation. Particularly, the phase separation of thickening agents palmitic acid and stearic acid with respect to the cross-linked PVP complexed with hydrogen peroxide was evaluated. The oral care compositions (4)-(6) were prepared by combining the ingredients/components according to Table 3. As indicated in Table 3, oral care composition (4) included fumed silica, oral care composition (5) included stearic acid, and oral care composition (6) included palmitic acid.

TABLE 3

Oral Care Compositions (4)-(6)

| Material | Oral Care Composition (4) | Oral Care Composition (5) | Oral Care Composition (6) |
|---|---|---|---|
| Propylene Glycol | 24.00% | 24.95% | 24.26% |
| PPO/PEO block copolymer | 24.01% | 24.96% | 24.25% |
| Sodium Metaphosphate | 15.00% | 15.00% | 15.00% |
| PEG/PPG copolymer | 7.50% | 7.50% | 7.50% |
| Cross-linked PVP complexed with HP | 16.50% | 16.50% | 16.50% |
| PVP | 2.00% | — | 2.00% |
| Fumed Silica | 3.50% | — | — |
| Stearic Acid | — | 3.00% | — |
| Palmitic Acid | — | — | 3.00% |
| Excipients (Anticalculus and/or Anti-tartar agent, Flavor, Surfactants, Sweeteners, Fluoride, Antioxidants) | Q.S | Q.S | Q.S |
| Total | 100% | 100% | 100% |

To evaluate the phase separation, each of the oral care compositions (4)-(6) was exposed to accelerated aging conditions (40° C.) for 13 weeks. After aging, each of the oral care compositions (4)-(6) was graded or assigned a score on a scale of 0 to 4 based on the observed phase separation. A score of '0' indicated no separation, a score of "1" indicated a trace amount of separation, a score of "2" indicated slight separation, a score of "3" indicated moderate separation, and a score of '4' indicated failure or separation. The results are summarized in Table 4.

TABLE 4

Separation Data for Oral Care Compositions (4)-(6)

| | Oral Care Composition (4) | Oral Care Composition (5) | Oral Care Composition (6) |
|---|---|---|---|
| Phase Separation | 2 | 0 | 0 |

As indicated in Table 4, both the oral care compositions (5) and (6) surprisingly and unexpectedly outperformed the oral care composition (4) including fumed silica, a conventional thickener used to prevent separation. Particularly, oral care compositions (5) and (6) exhibited no phase separation as compared to the control oral care composition (4), which include the conventional thickener.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. An oral care composition comprising:
   an orally acceptable vehicle;
   one or more sources of a peroxide whitening agent, wherein the source of the peroxide whitening agent is present in an amount of from about 9 weight % to about 23 weight % by weight of the composition; and
   one or more gelling agents, wherein the gelling agents comprise a fatty acid,
   wherein the one or more gelling agents is present in an amount of about 1.5 weight % to about 5 weight % by weight of the composition, and
   wherein the oral care composition comprises water in an amount of less than 3.0 weight % by weight of the composition.

2. The oral care composition according to claim 1, wherein the fatty acid comprises a C12-C28 fatty acid.

3. The oral care composition according to claim 1, wherein the fatty acid comprises at least one of lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, linoleic acid, arachidonic acid, palmitoleic acid, oleic acid, or mixtures thereof.

4. The oral care composition according to claim 1, wherein the fatty acid comprises a saturated fatty acid.

5. The oral care composition according to claim 1, wherein the fatty acid comprises an unsaturated fatty acid.

6. The oral care composition according to claim 1, wherein the fatty acid comprises at least one of palmitic acid, stearic acid, or mixtures thereof.

7. The oral care composition according to claim 1, wherein the gelling agents is present in an amount of from about 0.1 weight % to about 50 weight %.

8. The oral care composition according to claim 1, wherein the one or more gelling agents are substantially free of fatty alcohols.

9. The oral care composition according to claim 1, wherein the oral care composition comprises fatty alcohols in an amount of less than 5.0 weight %, less than 3.0 weight %, less than 1.0 weight %, less than 0.1 weight %, less than 0.05 weight %, less than 0.01 weight %, less than 0.005 weight %, less than 0.0001 weight %, based on a total weight of the oral care composition.

10. The oral care composition according to claim 1, wherein the oral care composition is substantially free of a fatty alcohol.

11. The oral care composition according to claim 1, wherein the oral care composition is a single phase oral care composition.

12. The oral care composition according to claim 1 wherein the peroxide whitening agent comprises hydrogen peroxide or one or more sources of hydrogen peroxide.

13. The oral care composition according to claim 1 wherein the peroxide whitening agent comprises at least one of hydrogen peroxide, a cross-linked PVP hydrogen peroxide complex, peroxides of alkali and alkaline earth metals, organic peroxy compounds, peroxy acids, pharmaceutically-acceptable salts thereof or mixtures thereof.

14. The oral care composition according to claim 1, wherein the peroxide whitening agent is a cross-linked PVP hydrogen peroxide complex.

15. A method for whitening teeth, comprising contacting a tooth surface of a subject in need thereof, with the oral care composition according to claim 1.

16. The oral composition of claim 1, wherein the oral composition is anhydrous.

\* \* \* \* \*